United States Patent [19]

Kindscher et al.

[11] 4,060,522
[45] Nov. 29, 1977

[54] SULFONAMIDO CONTAINING CARBOXYLIC ACIDS

[75] Inventors: Wolfgang Kindscher, Fussgoenheim; Martin Fischer, Ellerstadt; Karl Eicken, Wachenheim; Guenter Vitt, Mannheim, all of Germany

[73] Assignee: BASF Aktiengesellschaft, Ludwigshafen, Germany

[21] Appl. No.: 666,975

[22] Filed: Mar. 15, 1976

[30] Foreign Application Priority Data

Mar. 15, 1975 Germany .............................. 2511400

[51] Int. Cl.² .................... C07D 211/96; C23F 11/16

[52] U.S. Cl. ................................ 260/293.85; 544/158; 544/109; 544/110; 544/85; 260/268 S; 260/283 SA; 260/286 R; 260/294.8 R; 260/294.8 F; 260/326.42; 260/501.12; 260/514 H; 260/514 J; 260/518 R; 260/518 A; 260/519; 260/534 S; 260/534 M; 252/391; 21/2.7 R; 544/128; 544/124

[58] Field of Search ........... 260/247.1, 293.85, 556 A, 260/247.1 R, 286 R, 283 SA, 326.42, 501.12, 514 J, 514 H, 518 R, 518 A, 519, 246 B, 294.8 R, 534 S, 534 M

[56] References Cited

U.S. PATENT DOCUMENTS

| | | | |
|---|---|---|---|
| 3,506,711 | 4/1970 | Tesoro et al. ........................ | 260/556 |
| 3,661,917 | 5/1972 | Kaiser et al. ..................... | 260/293.73 |

*Primary Examiner*—Henry R. Jiles
*Assistant Examiner*—R. W. Ramsuer
*Attorney, Agent, or Firm*—Keil, Thompson & Shurtleff

[57] ABSTRACT

Amidosulfocarboxylic acids, their preparation from primary or secondary amines and chlorosulfocarboxylic acids, and their use as anticorrosive agents.

4 Claims, No Drawings

SULFONAMIDO CONTAINING CARBOXYLIC ACIDS

This invention relates to novel amidosulfocarboxylic acids.

There is always a risk of corrosion in numerous fields whenever iron and other iron-containing metals such as steel come into contact with water or with inorganic-/aqueous or organic/aqueous solutions, aqueous emulsions of the oil-in-water type or aqueous solids dispersions and similar systems containing appreciable amounts of water.

In most cases, the corrosive action of the said aqueous medium on machinery and apparatus, on tanks and tube walls and other structural elements of iron, iron alloys or steel, must be reduced or inhibited by the addition of anticorrosive substances. Some reduction in the tendency to corrode is frequently achieved simply by creating an alkaline pH either by the addition of alkali metal hydroxide, alkaline-reacting salts such as soda, borax and alkali metal phosphates, or by the addition of organic bases such as mono-, di- or triethanolamine and other aliphatic, aromatic, cycloaliphatic and heterocyclic amines.

However, an appreciable reduction in the corrosive action of the aqueous medium is achieved in this way only at pH's above 9.5 to 10. In many cases the effect is by no means satisfactory, particularly when the metal surface is to remain passive over a fairly long period after contact with the aqueous medium has ceased.

Genuine passivation is achieved, in suitable cases, by the use of oxidizing inorganic salts such as sodium nitrite, sodium chromate or nitric acid itself, but this method can seldom be utilized fully nowadays on account of the toxicity of said substances and effluent laws. Moreover, this method of effecting passivation by forming a film is seldom utilizable in the cases mentioned above. However, passivation effected by forming a film using suitable organic compounds, which, under the neutral to relatively strong alkaline conditions of present interest, are usually of an anionic or possibly non-ionic or not more than weakly cationic nature, is generally applicable.

Examples of anionic compounds are the alkali metal or amine salts of straight-chain aliphatic, saturated or unsaturated carboxylic acids, particular use having been made of said salts of oleic acid. Furthermore, the salts of aliphatic carboxylic acids containing carbonamide or sulfonamide groups, e.g. the salts of oleoylsarcoside or of alkanesulfonamidocarboxylic acids, have been known for many years to be very effective agents for preventing corrosion of iron and steel in aqueous media. More recently, as disclosed for example in German Published Application No. 1,298,672, optionally nuclear-substituted arylsulfonamidocarboxylic acids and salts thereof have been considered for this purpose; other compounds which have been known for a relatively long time to be suitable are simple alkyl-substituted benzoic acids or alkylaryl sulfonic acids.

However, these anionic compounds suffer from considerable disadvantages. Fatty acid salts, of which the salts of oleic acid have been particularly emphasized, possess a certain degree of sensitivity to water hardness and this greatly reduces the anticorrosive action (which does not satisfy highest requirements anyway) of the substances on iron and steel. The products containing carbonamide groups, such as the oleoyl sarcosides, are less sensitive to water hardness but have a tendency to foam which is difficult to control and which therefore restricts their use.

The said optionally nuclear-substituted arylsulfonamidocarboxylic acids and salts thereof only exhibit sufficiently low foaming properties and an anticorrosive action when they are alkylated at the amide nitrogen atom, which measure entails additional manufacturing expense. Furthermore, they must be based on aromatic sulfo compounds for the formation of sulfonamide groups, which is now less desirable for effluent reasons. The said alkane sulfonamidocarboxylic acids and their salts are also unsatisfactory on account of the demand for additional alkylation at the amide nitrogen atom, despite which the foaming activity is still too strong.

Of the non-ionic or weakly cationic anticorrosive agents generally known for many years but not specifically mentioned in more recent patents, particular examples are the alkylol amides of aliphatic carboxylic acids and their alkylol amine esters, e.g. oleic mono- or diethanolamide or oleic mono- or diisopropanol amide.

Compounds of a weakly cationic nature are the fatty acid esters of triethanolamine or triisopropanolamine, which compounds have been used in this field for many years. However, on account of their poor solubility in water these compounds can only be used in combination with the aforementioned anionic anticorrosive agents, or only in the oil phase of aqueous emulsions to be effective as the anticorrosive component of the emulsion.

It is an object of the invention to provide water-soluble or water-dispersible anionic corrosion inhibitors having a broad range of effectiveness and usefulness and, in particular, not exhibiting the aforementioned drawbacks.

We have now found compounds of formula I

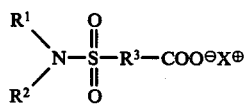

where $R^1$ denotes straight-chain or branched-chain, saturated or olefinically or acetylenically unsaturated alkyl of from 1 to 18 or 3 to 18 carbon atoms respectively and optionally containing combined methoxy or ethoxy groups, or $R^1$ denotes cycloalkyl of from 5 to 12 members, phenyl optionally substituted by alkyl of from 1 to 3 carbon atoms, methoxy, ethoxy or halogen, or $R^1$ denotes phenylalkyl containing 1 to 6 carbon atoms in the alkyl group, $R^2$ denotes hydrogen or $R^1$, $R^1 + R^2$ denote, together with the nitrogen atom, a heterocyclic saturated ring having 5 or 6 members, $R^3$ denotes substituted or unsubstituted alkylene of from 2 to 5 carbon atoms and $X^+$ denotes an alkali metal or optionally substituted ammonium cation or proton.

We have also found that these compounds and in particular the alkali metal and optionally substituted ammonium salts are eminently suitable for use as metal processing agents exhibiting maximum anticorrosive action, low tendency to foam and good lubricating properties.

Preparation of our novel compounds is simple and is effected by reacting amines of formula II

where $R^1$ and $R^2$ have the meanings stated in formula I, with chlorosulfonylcarboxylic acid esters of formula III

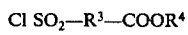

where $R^3$ has the meaning given in formula I and $R^4$ denotes $C_{1-5}$ alkyl, in the presence of alkaline reacting compounds, and converting, by known methods, the esters formed into the free acid or its alkali metal or optionally substituted ammonium salts.

Starting materials for the preparation of the compounds of the invention are amines of formula II, examples of which are the following primary amines:

methylamine, ethylamine, n-propylamine, isopropylamine, n-butlyamine, isobutylamine, n-hexylamine, n-octylamine, isomeric hexylamine mixtures, 2-ethyl-n-hexylamine, 2-methyl-n-butylamine, methoxyethylamine, cyclohexylamine, n-dodecylamine, stearylamine, oleylamine, 2-methyl-butyn-3-yl-amine, aniline, toluidine, anisidine, phenetidine, benzylamine, phenylethylamine, phenyl-n-butylamine and phenyl-n-hexylamine;

and the following secondary amines:

dimethylamine, diethylamine, di-n-propylamine, diisopropylamine, di-n-butylamine, diisobutylamine, diisoamylamine, di-n-hexylamine, di-n-octylamine, didocecylamine, distearylamine, dioleylamine, dihexylamine (isomeric mixtures), di-[2-ethyl-n-hexyl]-amine, di-[2-methyl-n-butyl]-amine, N-methyl-N'-n-butylamine, N-methyl-N'-isobutylamine, piperidine, piperazine, pyrrolidine, morpholine, N-methylaniline and N-ethylaniline.

Further starting materials are the chlorosulfonylcarboxylic acid esters of formula III. Suitable esters are, for example, methyl, ethyl and isopropyl 3-chlorosulfonyl-propionates, methyl, ethyl and isopropyl 3- or 4-chlorosulfonylbutyrates and the corresponding esters of chlorosulfonyl-n-valeric acid and chlorosulfonyl-isovaleric acid.

These starting compounds may be prepared by photosulfochlorination of the corresponding carboxylic acid esters.

Suitable alkaline reacting compounds required during the reaction of the amines with the chlorosulfonylcarboxylic acid esters or during use of the reaction products formed are alkaline earth metal hydroxides and alkali metal hydroxides or any of the above amines of formula II; if amines are employed, they have to be used in molar excess. However, we prefer to use inorganic bases such as sodium hydroxide.

Suitable bases for the formation of salts with the amidosulfocarboxylic acids are any inorganic or organic bases capable of forming water-soluble products. By water-soluble we mean the colloid, emulsoid or suspensoid state. Salts may be formed with, for example, alkalies or, preferably, organic bases such as mono-, di- and trimethylamines, mono-, di- and triethylamines, mono-, di- and triisopropylamines, mono-, di- and triisobutylamines, 2-methoxyethylamine, 3-methoxypropylamine, 2-ethylhexylamine, mono-, di- and triethanolamine, 3-aminopropanol, cyclohexylamine, N,N-dimethylcyclohexylamine, morpholine, pyridine, quinoline, ethylene diamine, diethylene triamine, pentaethylene hexamine and also ethoxylated or propoxylated primary amines.

For salt formation, the reactants may be present in stoichiometric amounts or one of the reactants may be used in an excess of up to 200% molar.

To form the sulfonamide, the molar ratio of the two components (chlorosulfonylcarboxylic acid ester of formula III and amine of formula II) may be from 1:2.5 to 1:1, although we prefer to use the two reactants in approximately equimolar amounts. The hydrogen chloride liberated during the reaction may be combined, depending on the excess of the basic reactant, either by the use of excess amine or by the addition of a further base such as a tertiary amine, an alkali metal hydroxide or alkaline earth metal hydroxide.

The reaction may be carried out by simultaneous mixing all three reactants or by placing one or two of the reactants in the reaction vessel and then adding the other two or the third reactant. For example, the amine may be initially placed in the vessel and the chlorosulfonylcarboxylic acid ester and the alkaline-reacting compound may be simultaneously fed thereto. The best yields are, however, obtained in the reaction of approximately equimolar amounts of sulfochloride and amine when the amine is initially placed in the vessel, half the molar amount of the appropriate chlorosulfonylcarboxylic acid ester is added, and the remainder of said chlorosulfonylcarboxylic acid ester and 1 mole of, say, an inorganic base are simultaneously added from different feed vessels. Suitable reaction media are water and organic solvents, and the reactants may be in homogeneous phase or in two phases, and dissolved, emulsified or suspended. In a preferred embodiment the reactants are present in two phases in aqueous medium. The reactants may be used diluted or undiluted and it has been found convenient to use a concentration of from 0.2 to 5.0 moles/l, the best yields being obtained at concentrations of from 1.0 to 3.0 moles/l. Sulfonamide formation takes place over the entire alkaline range; suitable pH's are from 7 to 9 with pH's between 8 and 8.5 giving the best reaction. Sulfonamide formation is satisfactory over a temperature range of from −40° to +40° C, the best yields being obtained at temperatures ranging from −20° to +20° C, and in a preferred embodiment the temperatures are maintained between −5° and +5° C. The time taken for the sulfonamide to form depends to a marked degree, particularly in two-phase systems, on the intensity with which the components are mixed, the shortest reaction times being ensured when the stirrer blade or segment is positioned at the boundary between the two phases of the reaction mixture.

The amidosulfocarboxylic acid ester may be isolated by conventional working-up methods and converted to the amidosulfocarboxylic acid by known saponification methods.

In a preferred embodiment, however, the amidosulfocarboxylic acid ester is not isolated but is directly saponified by the addition of further amine, alkaline, metal hydroxide or alkaline earth metal hydroxide. Temperatures of from 60° to 100° C are required for this operation, the best yields being obtained at temperatures of from 75° to 85° C. Saponification takes place with satisfactory yields over the entire alkaline pH range, the reaction times being particularly short under strongly alkaline conditions. The amine, alkali metal or alkaline earth metal hydroxide may be present in an excess of up to 100% molar, the best results being obtained at an excess of from 10 to 20%.

The amidosulfocarboxylic acids obtained after acidification of the amidosulfocarboxylic acid salts with commercial mineral acids may then be isolated by conventional working-up methods and provide the corrosion inhibitors of the invention in a simple manner when neutralized with the said organic or inorganic bases.

As stated above, the alkali metal or alkaline earth metal salts of the amidosulfocarboxylic acids may be primarily formed during ester saponification. The salts with organic amines may be readily prepared by taking free amidosulfocarboxylic acid and mixing into it the stoichiometric amount or a superstoichiometric amount of the appropriate amine.

In this case it is usually necessary to warm and stir the mixture until the salt-forming reaction begins. Thorough stirring and, if necessary, effective cooling must be employed to prevent the temperature of the mixture from rising too high on account of the heat of neutralization generated. Particularly strong heat generation may be avoided by preheating the amidosulfocarboxylic acid to about 50° C and then adding the amine thereto in small portions with stirring, each portion being added only when the temperature has begun to sink, after the addition of the previous portion, below the preferred average temperature level of about 50° C.

The concentrations at which the anticorrosive agents are used depend on the nature of the liquids which will come into contact with the iron or iron-containing metal.

Applications of this kind are, for example, refrigerating and hydraulic liquids, water-soluble metalworking and machining liquids free from mineral oils, metalworking and machining emulsions, drilling fluids, grinding and polishing emulsions or dispersions, and metal cleaners of various kinds. Other liquids are anticorrosive surface treating agents such as anticorrosive emulsions and water-based passivating solutions. The agents may also be added to process waters in the chemical industry and other industries in which such water contacts iron and steel.

Depending on the application, the salts of amidosulfocarboxylic acids to be used according to the invention are employed in concentrations of from 0.5 to 5.0% by weight or in some cases more, based on the particular liquid medium being treated.

EXAMPLE 1a

N-(2-ethyl-n-hexyl)-amidosulfopropionic Acid (1)

To 25.8 parts of 2-ethyl-n-hexylamine and 120 parts of water there are added dropwise, at 0° C with stirring, initially 18.65 parts of methyl 3-chlorosulfonylpropionate and then, simultaneously from separate dropping funnels, 18.65 parts of methyl 3-chlorosulfonylpropionate and 54 parts of 14.8% caustic soda solution. The mixture is then stirred for 1 hour at 0° C and for half an hour at room temperature; 8.8 parts (0.22 mole) of sodium hydroxide are added and the mixture is heated for 2 hours at 70° C. The reaction mixture is acidified to a pH of 1 with a 2N solution of $H_2SO_4$, and the resulting mixture is extracted with carbon tetrachloride. On removal of the solvent, there are obtained from the organic phase 48.0 parts (90.6% of theory) of N-2-ethyl-n-hexyl-3-amidosulfopropionic acid in the form of a yellow oily liquid which solidifies to a wax on storage.

| Analysis results | C | H | N | SN+ | AN++ |
|---|---|---|---|---|---|
| Found: | 50.1 | 9.1 | 5.4 | 212 | 147 |
| Calculated: | 49.4 | 8.8 | 5.3 | 211 | 211 |

+saponification number
++acid number.

EXAMPLE 1b

Sodium-N-(2-ethyl-n-hexyl)-3-amidosulfopropionate

I. 187 Parts of methyl 3-chlorosulfonylpropionate are added dropwise at 0° C with stirring to 129 parts of 2-ethyl-n-hexylamine, 101 parts of triethylamine and 500 parts of methylene chloride. Stirring is continued for 2 hours at 0° C and the reaction mixture is then washed until neutral with 80 parts of water, 50 parts of a 2N solution of HCl and 50 parts of water. After removal of the solvent the crude product is distilled. There are obtained 212 parts (76% of theory) of methyl N-(2-ethyl-n-hexyl)-3-amidosulfopropionate which boils at 197° C/1.2 mm.

II. 204 parts of methyl N-(2-ethyl-n-hexyl)-3-amidosulfopropionate are mixed with 350 parts of $H_2O$ and 29.2 parts of sodium hydroxide, and the mixture is stirred for 1 hour at 80° C. The reaction mixture is evaporated to dryness. There are obtained 210 parts (100% of theory) of sodium-N-(2-ethyl-n-hexyl)-3-amidosulfopropionate.

| Analysis results | C | H | O | N | S | Na |
|---|---|---|---|---|---|---|
| Found: | 45.7 | 7.5 | 22.5 | 4.8 | 11.3 | 8.2 |
| Calculated: | 46.0 | 7.7 | 22.3 | 4.9 | 11.2 | 8.0 |

EXAMPLE 2

N-(3-phenyl-n-butyl)-3-amidosulfopropionic Acid (2)

I. 126 Parts of methyl 3-chlorosulfonylpropionate are added dropwise at 0° C with stirring to 100 parts of (3-phenyl-n-butyl)-amine, 68 parts of triethylamine and 340 parts of methylene chloride. Stirring is continued for a further 1.5 hours at 0° C and the reaction mixture is then washed with 2N HCl and $H_2O$ until neutral. After removal of the solvent there are obtained 169 parts (84.5% of theory) of methyl N-(3-phenyl-n-butyl)-3-amidosulfopropionate, m.p. (after recrystallization from ethanol): 61° C.

II. 121 Parts of methyl N-(3-phenyl-n-butyl)-3-amidosulfopropionate, 275 parts of water and 16.2 parts of sodium hydroxide are stirred for 1 hour at 80° C. The reaction mixture is acidified with 22% HCl (pH 1 to 2) and the precipitated acid is filtered off. After washing with 100 parts of water and drying at 40° C/25 mm there are obtained 113 parts of N-(3-phenyl-n-butyl)-3-amidosulfopropionic acid (98% of theory), m.p. 89°–91° C.

| Analysis results | C | H | O | N | S | SN | AN |
|---|---|---|---|---|---|---|---|
| Found: | 54.3 | 6.3 | 21.1 | 4.6 | 10.2 | 202 | 193 |
| Calculated: | 54.75 | 6.7 | 22.45 | 4.9 | 11.2 | 197 | 197 |

EXAMPLE 3

N-(phenylhexyl)-3-amidosulfopropionic Acid (isomers) (3)

I. 109.5 Parts of methyl 3-chlorosulfonylpropionate are added dropwise at 5° C with stirring to 104 parts of N-(phenylhexyl)-amine (isomers), 59 parts of triethylamine and 340 parts of $CH_2Cl_2$. The mixture is then stirred for a further 2 hours at 5° C and the reaction mixture is thereupon washed with 2N HCl and water until neutral. After removal of the solvent there are obtained 167.5 parts (87% of theory) of methyl N-(phenylhexyl)-3-amidosulfopropionate (isomers) as a yellow oil.

II. 167.5 parts of methyl N-(phenylhexyl)-3-amidosulfopropionate (isomers), 280 parts of water and 20.5 parts of sodium hydroxide are stirred for 1.5 hours at 80° C and then acidified to a pH of 2 with 20% HCl. Following extraction with benzene and removal of the solvent there are obtained 119 parts (75% of theory) of N-(phenylhexyl)-3-amidosulfopropionic acid (isomers) in the form of a pale brown, tough mass.

Analysis results

| | C | H | O | N | S | SN | AN |
|---|---|---|---|---|---|---|---|
| Found: | 57.2 | 7.6 | 20.5 | 4.3 | 10.4 | 173 | 184 |
| Calculated: | 57.5 | 7.4 | 20.4 | 4.5 | 10.2 | 179 | 179 |

EXAMPLE 4

N-benzyl-3-amidosulfopropionic Acid (4)

I. 187 Parts of methyl 3-chlorosulfonylpropionate are added dropwise at 0° C with stirring to 107 parts of benzylamine, 101 parts of triethylamine and 400 parts of methylene chloride. The mixture is stirred for a further 3 hours at 0° C and is then washed with water until neutral. After removal of the solvent there are obtained 249.2 parts (97% of theory) of methyl N-benzyl-3-amidosulfopropionate as a pale yellow, crystalline product, m.p. 74°-77° C (recrystallized from isopropanol).

II. 192.9 Parts of methyl N-benzyl-3-amidosulfopropionate and 380 parts of 2N caustic soda solution are stirred for 1 hour at 80° C. The reaction mixture is acidified with HCl to a pH of 2 and the precipitated acid is filtered off. There are obtained 178.2 parts (73.2% of theory) of N-benzyl-3-amidosulfopropionic acid in the form of a white crystalline product, m.p. 150°-153° C.

Analysis results

| | C | H | O | N | S | SN | AN |
|---|---|---|---|---|---|---|---|
| Found: | 49.1 | 5.2 | 26.6 | 6.1 | 13.0 | 234 | 237 |
| Calculated: | 49.4 | 5.4 | 26.3 | 5.8 | 13.1 | 231 | 231 |

EXAMPLE 5

N-(2-phenylethyl)-3-amidosulfopropionic Acid (5)

I. 18.7 Parts of methyl 3-chlorosulfonylpropionate are added dropwise at 0° C with stirring to 10.9 parts of 2-phenylethylamine, 10.1 parts of triethylamine and 100 parts of benzene. Stirring is continued for a further 2 hours at 0° C and the reaction mixture is then washed with water until neutral. On removal of the solvent and following recrystallization from ethanol there are obtained 17.4 parts (67% of theory) of methyl N-(2-phenylethyl)-3-amidosulfopropionate, m.p. 82° C.

II. 5.2 Parts of methyl N-(2-phenylethyl)-3-amidosulfopropionate and 50 parts of 1N caustic soda solution are heated with stirring for 1 hour at 80° C. The mixture is then acidified with HCl to a pH of 1 and the precipitated acid is filtered off.

There are obtained 4.3 parts (81.5% of theory) of N-(2-phenylethyl)-3-amidosulfopropionic acid, m.p. 117° C.

Analysis results

| | C | H | O | N | S | SN | AN |
|---|---|---|---|---|---|---|---|
| Found: | 51.6 | 6.0 | 24.6 | 5.2 | 12.6 | 215 | 223 |
| Calculated: | 51.4 | 5.8 | 24.9 | 5.4 | 12.5 | 218 | 218 |

EXAMPLE 6

N-(2-methyl-n-butyl)-3-amidosulfopropionic Acid (6)

I. 18.7 Parts of methyl 3-chlorosulfonylpropionate are added dropwise at 0° C to 8.7 parts of 2-methyl-n-butylamine, 10.1 parts of triethylamine and 100 parts of methylene chloride. The mixture is stirred for 4 hours at room temperature and is then washed with $H_2O$ until neutral. After removal of the solvent there are obtained 12.6 parts (53.2% of theory) of methyl N-(2-methyl-n-butyl)-3-amidosulfopropionate.

II. 12.6 Parts of methyl N-(2-methyl-n-butyl)-3-amidosulfopropionate and 53 parts of 1N caustic soda solution are heated for 2 hours at 80° C. The reaction mixture is acidified to a pH of 2 with concentrated hydrochloric acid and the acid is extracted with $CH_2Cl_2$. After removal of the solvent and recrystallization from 100 parts of benzene, there are obtained 6.5 parts (55% of theory) of N-(2-methyl-n-butyl)-3-amidosulfopropionic acid, m.p. 98°-99° C.

Analysis results

| | C | H | O | N | S | SN | AN |
|---|---|---|---|---|---|---|---|
| Found: | 43.3 | 7.7 | 28.6 | 6.3 | 14.2 | 246 | 257 |
| Calculated: | 43.1 | 7.6 | 28.6 | 6.3 | 14.3 | 251 | 251 |

EXAMPLE 7

N-(2-methylbut-3-ynyl)-3-amidosulfopropionic Acid (7)

I. 74.8 Parts of methyl 3-chlorosulfonylpropionate are added dropwise with stirring at from 0° to 5° C to 23.6 parts of 2-(methylbut-3-ynyl)-amine, 40.4 parts of triethylamine and 100 parts of methylene chloride. Stirring is continued for a further 2 hours at room temperature and the reaction mixture is then washed until neutral with 20 parts of 0.5 N HCl and 60 parts of water. From the organic phase there are obtained, after removal of the solvent and recrystallization from isopropanol, 61 parts (72.8% of theory) of methyl N-(2-methylbut-3-ynyl)-3-amidosulfopropionate, m.p. 72°-73° C.

II. 60 Parts of methyl N-(2-methylbut-3-ynyl)-3amidosulfopropionate, 40 parts of $H_2O$ and 11.2 parts of sodium hydroxide are stirred for 1 hour at 80° C. The reaction mixture is acidified with HCl to a pH of 1 to 2 and the precipitate is filtered off.

There are obtained 39.1 parts of N-(2-methylbut-3-ynyl)-3-amidosulfopropionic acid, m.p. 107°-109° C.

Analysis results

| | C | H | O | N | S | SN | AN |
|---|---|---|---|---|---|---|---|
| Found: | 43.6 | 6.2 | 29.4 | 6.5 | 14.3 | 260 | 249 |
| Calculated: | 43.9 | 5.9 | 29.2 | 6.4 | 14.6 | 256 | 256 |

EXAMPLE 8

N-phenyl-3-amidosulfopropionic Acid (8)

I. 18.7 parts of methyl 3-chlorosulfonylpropionate are added dropwise at 0° C with stirring to 9.3 parts of aniline, 10.1 parts of triethylamine and 100 parts of methylene chloride. The mixture is stirred for a further 4 hours and then washed with 100 parts of $H_2O$. After removal of the solvent and recrystallization from ethanol there are obtained 17.2 parts (68.5% of theory) of methyl N-phenyl-3-amidosulfopropionate, m.p. 81°–83° C.

II. 12 Parts of methyl N-phenyl-3-amidosulfopropionate are heated with 47.5 parts of 1N caustic soda solution for 2 hours at 80° C. The reaction mixture is acidified with 50 parts of concentrated HCl. The precipitated acid is filtered off and washed with pentane.

There are obtained 7.5 parts (65.7% of theory) of N-phenyl-3-amidosulfopropionic acid, m.p. 79°–81° C.

Analysis results

|  | C | H | O | N | S | SN | AN |
|---|---|---|---|---|---|---|---|
| Found: | 48.9 | 5.4 | 26.6 | 5.9 | 11.8 | 249 | 254 |
| Calculated: | 47.0 | 4.8 | 28.0 | 6.1 | 13.9 | 245 | 245 |

EXAMPLE 9

N,N-(di-2-ethyl-n-hexyl)-3-amidosulfopropionic Acid (9)

I. 18.7 Parts of methyl 3-chlorosulfonylpropionate are added dropwise with stirring at from 0° to 5° C to 24.1 parts of di-2-ethyl-n-hexylamine, 10.1 parts of triethylamine and 150 parts of methylene chloride. Stirring is continued for a further 4 hours and the reaction mixture is then washed with 50 parts of water until neutral. After removal of the solvent there are obtained 32.3 parts (83.3% of theory) of methyl N,N-(di-2-ethyl-n-hexyl)-3-amidosulfopropionate.

II. 32.3 Parts of methyl N,N-(di-2-ethyl-n-hexyl)-3-amidosulfopropionate and 42 parts of 2N caustic soda solution are heated with stirring for 3 hours at 80° C. The reaction mixture is acidified with 10 parts of concentrated HCl to a pH of 3 and is extracted with $CH_2Cl_2$. After removal of the solvent there are obtained 26.7 parts (88.5% of theory) of N,N-(di-2-ethyl-n-hexyl)-3-amidosulfopropionic acid as a brown oil.

Analysis results

|  | SN | AN |
|---|---|---|
| Found: | 216 | 208 |
| Calculated: | 212 | 212 |

N,N-(di-n-butyl)-3-amidosulfopropionic Acid (10)

To 25.8 parts of di-n-butylamine and 100 parts of water there are added dropwise at 0° C, with stirring, 18.65 parts of methyl 3-chlorosulfonylpropionate followed by simultaneous feed from separate dropping funnels of 18.65 parts of methyl 3-chlorosulfonylpropionate and 54 parts of 14.8% caustic soda solution. Stirring is continued for a further hour at 0° C and then for 4 hours at room temperature; 8.8 parts of sodium hydroxide are added and the mixture is heated for 4 hours at 60° C. The reaction mixture is then acidified with 2N $H_2SO_4$ to a pH of 1 and is extracted with carbon tetrachloride. Following concentration of the dried $CCl_4$ phase at 60° C/1 mm there are obtained 23 parts (43.4% of theory) of N,N-(di-n-butyl)-3-amidosulfopropionic acid as a white crystalline product, m.p. 78°–80° C (after recrystallization from cyclohexane).

Analysis results

|  | C | H | O | N | S | SN | AN |
|---|---|---|---|---|---|---|---|
| Found: | 50.4 | 8.6 | 23.2 | 5.7 | 11.8 | 230 | 203 |
| Calculated: | 49.8 | 8.7 | 24.15 | 5.3 | 12.05 | 212 | 212 |

EXAMPLE 10b

N,N-(di-n-butyl)-3-amidosulfopropionic Acid (10)

I. 18.7 Parts of methyl 3-chlorosulfonylpropionate are added dropwise at from 0° to 5° C with stirring to 12.9 parts of di-n-butylamine, 10.1 parts of triethylamine and 150 parts of methylene chloride. Stirring is continued for a further 4 hours and the reaction mixture is then washed with water until neutral. After removal of the solvent there are obtained 23.2 parts (83% of theory) of methyl N,N-(di-n-butyl)-3-amidosulfopropionate.

II. 23.3 Parts of methyl N,N-(di-n-butyl)-3-amidosulfopropionate and 42 parts of 2N caustic soda solution are heated for 1 hour at 80° C and the mixture is then acidified with 7 parts of concentrated HCl to a pH of 3. The mixture is extracted with $CH_2Cl_2$ and there are obtained, after recrystallization from n-heptane, 6.9 parts (31.5% of theory) of N,N-(di-n-butyl)-3-amidosulfopropionate.

Analysis results

|  | SN | AN |
|---|---|---|
| Found: | 220 | 206 |
| Calculated: | 212 | 212 |

EXAMPLE 11

N-(n-butyl)-3-amidosulfopropionic Acid

To 14.6 parts of n-butylamine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for a further hour at 0° C and 4 hours at room temperature; 8.8 parts of sodium hydroxide are added and the mixture is heated for 4 hours at 60° C. The reaction mixture is acidified with 2N $H_2SO_4$ solution to a pH of 1. The resulting precipitate is filtered off, washed with 100 parts of water and dried at 40° C in a vacuum drying cabinet. This product and the product obtained from the mother liquor by extraction with ether total 24.7 parts (59.1% of theory) of N-(n-butyl)-3-amidosulfopropionic acid (white crystals), m.p. 136°–138° C (recrystallized from 80% alcohol).

Analysis results

|  | C | H | O | N | S | AN | SN |
|---|---|---|---|---|---|---|---|
| Found: | 40.1 | 7.0 | 30.2 | 6.8 | 15.1 | 272 | 260 |
| Calculated: | 40.2 | 7.2 | 30.6 | 6.7 | 15.3 | 268 | 268 |

EXAMPLE 12

N-ethyl-3-amidosulfopropionic Acid

To 9 parts of ethylamine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for 1 hour at 0° C and 4 hours at room temperature; 8.8 parts of sodium hydroxide are added and the mixture is heated at 60° C for 4 hours. The reaction mixture is then shaken with ether and the aqueous phase is acidified with 2N $H_2SO_4$ solution to a pH of 1 and concentrated at 60° C/20 mm. When the residue is extracted with ether there are obtained, after removal of the ether, 4.1 parts (11.3% of theory) of N-ethyl-3-amidosulfopropionic acid in the form of a white crystalline product, m.p. 101°–104° C.

Analysis results

|  | C | H | O | N | S | SN | AM |
|---|---|---|---|---|---|---|---|
| Found: | 33.5 | 6.1 | 35.2 | 8.0 | 17.3 | 316 | 305 |
| Calculated: | 33.1 | 6.1 | 35.4 | 7.7 | 17.7 | 310 | 310 |

EXAMPLE 13

N-isopropyl-3-amidosulfopropionic Acid

To 11.8 parts of isopropylamine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for a further hour at 0° C and 4 hours at room temperature; 8.8 parts of sodium hydroxide are added and the mixture is heated at 60° C for 4 hours. The reaction mixture is acidified with a 2N $H_2SO_4$ solution to a pH of 1 and the resulting precipitate is filtered off, washed with 100 parts of water and dried (40° C/25 mm). This product and the product obtained from the NaCl-saturated aqueous phase by extraction with ether total 15.5 parts (39.7% of theory) of N-isopropyl-3-amidosulfopropionic acid, m.p. 125° C (after recrystallization from isopropanol).

Analysis results

|  | C | H | O | N | S | SN | AN |
|---|---|---|---|---|---|---|---|
| Found: | 37.2 | 6.7 | 32.2 | 7.4 | 16.2 | 291 | 282 |
| Calculated: | 36.9 | 6.7 | 32.8 | 7.2 | 16.4 | 288 | 288 |

EXAMPLE 14

N-isobutyl-3-amidosulfopropionic Acid

To 14.6 parts of isobutylamine and 100 parts of water there are added dropwise at 0° C, with stirring 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for a further hour at 0° C and 4 hours at room temperature; 8.8 parts of sodium hydroxide are added and the mixture is heated at 60° C for 4 hours. The reaction mixture is acidified with a 2N $H_2SO_4$ solution to a pH of 1 and the resulting precipitate is filtered off, washed with 100 parts of water and dried at 40° C/25 mm.

Yield: 24.6 parts (59% of theory) of white crystalline N-isobutyl-3-amidosulfopropionic acid, m.p. 132°–134° C (after recrystallization from $H_2O$).

Analysis results

|  | C | H | O | N | S | SN | AN |
|---|---|---|---|---|---|---|---|
| Found: | 40.7 | 7.2 | 30.1 | 7.1 | 15.0 | 270 | 253 |
| Calculated: | 40.2 | 7.2 | 30.6 | 6.7 | 15.3 | 268 | 268 |

EXAMPLE 15

N-methyl-N-n-butyl-3-amidosulfopropionic Acid

To 17.4 parts of N-methyl-n-butylamine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for a further hour at 0° C and for 4 hours at room temperature; 8.8 parts of sodium hydroxide are added and the mixture is heated at 60° C for 4 hours. The reaction mixture is acidified with a 2N solution of $H_2SO_4$ to a pH of 1, saturated with NaCl and extracted with ether. The dried ether phase is concentrated at 60° C/0.5 mm to give 14.0 parts (31.4% of theory) of N-methyl-N-n-butyl-3-amidosulfopropionic acid, m.p. 76°–78° C (recrystallized from cyclohexane/isopropanol).

Analysis results

|  | C | H | O | N | S | SN | AN |
|---|---|---|---|---|---|---|---|
| Found: | 43.3 | 7.6 | 28.6 | 6.6 | 14.0 | 281 | 244 |
| Calculated: | 43.1 | 7.6 | 28.7 | 6.3 | 14.3 | 251 | 251 |

EXAMPLE 16

N-methyl-N-isobutyl-3-amidosulfopropionic Acid

To 17.4 parts of N-methylisobutylamine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for a further hour at 0° C and 4 hours at room temperature; 8.8 parts of sodium hydroxide are added and the mixture is stirred at 60° C for 4 hours. The reaction mixture is shaken with carbon tetrachloride and the aqueous phase is acidified with 2N $H_2SO_4$ solution to a pH of 1. The free N-methyl-N-isobutyl-3-amidosulfopropionic acid is extracted with ether to give, on removal of the solvent at 60° C/1 mm, 18.7 parts (41.9% of theory) of said product in the form of white crystals, m.p. 75°–76° C.

Analysis results

|  | C | H | O | N | S | SN | AN |
|---|---|---|---|---|---|---|---|
| Found: | 43.1 | 7.5 | 28.8 | 6.2 | 14.2 | 261 | 250 |
| Calculated: | 43.1 | 7.6 | 28.7 | 6.3 | 14.3 | 251 | 251 |

EXAMPLE 17

N-methyl-N-n-butyl-3-amidosulfopropionic Acid

To 17.4 parts of N-methyl-n-butylamine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for 1 hour at 0° C and 4 hours at room temperature; 8.8 parts of caustic soda are added and the mixture is stirred at 60° C for 4 hours. The reaction mixture is shaken with CCl₄ and the aqueous phase is acidified with a 2N solution of H₂SO₄ to a pH of 1. The free N-methyl-N-n-butyl-3-amidosulfopropionic acid is extracted with ether to give, on removal of the solvent at 60° C/1 mm, 11.1 parts (24.9% of theory) of said product in the form of white crystals; m.p. 74°–76° C.

| Analysis results | C | H | O | N | S | SN | AN |
|---|---|---|---|---|---|---|---|
| Found: | 43.3 | 7.4 | 29.0 | 6.2 | 14.1 | 270 | 245 |
| Calculated: | 43.1 | 7.6 | 28.7 | 6.3 | 14.3 | 251 | 251 |

EXAMPLE 18

N-cyclohexyl-3-amidosulfopropionic Acid

To 19.8 parts of cyclohexylamine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for a further hour at 0° C and then for 4 hours at room temperature; 8.8 parts of sodium hydroxide are added and stirring is continued for 4 hours at 60° C. The reaction mixture is shaken with CCl₄ and the aqueous phase is acidified with a 2N H₂SO₄ solution to a pH of 1. The free N-cyclohexyl-3-amidosulfopropionic acid is extracted with ether to give, on removal of the solvent at 60° C/1mm, 17.0 parts (36.2% of theory) of said product in the form of white crystals, m.p. 121°–122° C (recrystallized from H₂O).

| Analysis results | C | H | O | N | S | SN | AN |
|---|---|---|---|---|---|---|---|
| Found: | 46.1 | 7.4 | 27.0 | 6.3 | 13.5 | 263 | 241 |
| Calculated: | 46.0 | 7.2 | 27.2 | 6.0 | 13.6 | 239 | 239 |

EXAMPLE 19

N-(2-methoxyethyl)-3-amidosulfopropionic Acid

To 15 parts of 2-methoxyethylamine and 100 parts of H₂O there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for 1 hour at 0° C and 4 hours at room temperature; 8.8 parts of sodium hydroxide are added and the mixture is heated at 60° C for 4 hours. The reaction mixture is shaken with CCl₄ and the aqueous phase is acidified with a 2N solution of H₂SO₄ to a pH of 1. It is then evaporated to dryness and the N-(2-methoxyethyl)-3-amidosulfopropionic acid is extracted with ether to give, on removal of the ether, 4.2 parts (10% of theory) of the desired compound as a white waxy product, m.p. 70°–72° C (recrystallized from cyclohexane containing 5% of isopropanol).

| Analysis results | C | H | O | N | S | SN | AN |
|---|---|---|---|---|---|---|---|
| Found: | 34.3 | 6.2 | 37.7 | 6.7 | 14.7 | 287 | 261 |
| Calculated: | 34.1 | 6.2 | 37.9 | 6.6 | 15.2 | 266 | 266 |

EXAMPLE 20

3-piperidylsulfopropionic Acid

To 17 parts of piperidine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for 1 hour at 0° C and 4 hours at room temperature; 8.8 parts of sodium hydroxide are added and the mixture is heated for 5 hours at 80° C. The reaction mixture is acidified with a 2N solution of H₂SO₄ to a pH of 1, evaporated to dryness and extracted with ether. There are obtained from the ether phase, after removal of the solvent, 4.1 parts of 3-piperidylsulfopropionic acid (9.3% of theory) in the form of a white crystalline product capable of recrystallization from water. Its melting point is 111° to 113° C (after recrystallization from H₂O).

| Analysis results | C | H | O | N | S | SN | AN |
|---|---|---|---|---|---|---|---|
| Found: | 43.5 | 6.9 | 28.9 | 6.5 | 14.2 | 266 | 249 |
| Calculated: | 43.4 | 6.8 | 29.0 | 6.3 | 14.5 | 254 | 254 |

EXAMPLE 21

3-pyrrolidinylsulfopropionic Acid

To 14.2 parts of pyrrolidine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for 1 hour at 0° C and 4 hours at room temperature; 8.8 parts of sodium hydroxide are added and the mixture is heated at 80° C for 5 hours. The reaction mixture is shaken with CCl₄ and the aqueous phase is acidified with 2N H₂SO₄ solution to a pH of 1 and evaporated to dryness. By extraction with ether and removal of the ether from the organic phase there are obtained 3.1 parts (7.5% of theory) of 3-pyrrolidinylsulfopropionic acid in the form of a white waxy product.

| Analysis results | C | H | O | N | S | AN | SN |
|---|---|---|---|---|---|---|---|
| Found: | 41.3 | 6.4 | 30.5 | 6.7 | 14.3 | 194 | 316 |
| Calculated: | 40.6 | 6.3 | 30.85 | 6.8 | 15.45 | 271 | 271 |

EXAMPLE 22

N,N-(di-2-methoxyethyl)-3-amidosulfopropionic Acid

To 26.6 parts of di-2-methoxyethylamine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for 1 hour at 0° C and 4 hours at room temperature; 8.8 parts of sodium hydroxide are added and the mixture is heated for 8 hours at 70° C. The alkaline reaction mixture is shaken with CCl₄ and the aqueous phase is acidified with a 2N solution of H₂SO₄ to a pH of 1 and concentrated to dryness. After extraction with ether there are obtained 2.4 parts (4.5% of theory) of N,N-(di-2-methoxyethyl)-3-amidosulfopropionic acid in the form of a colorless oil.

|  | C | H | O | N | S | SN | AN |
|---|---|---|---|---|---|---|---|
| Found: | 40.5 | 7.1 | 35.1 | 5.0 | 11.7 | 354 | 148 |
| Calculated: | 40.2 | 7.05 | 35.65 | 5.2 | 11.9 | 208 | 208 |

EXAMPLE 23

N-ethyl-N-n-butyl-3-amidosulfopropionic Acid

To 20.2 parts of N-ethyl-n-butylamine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for 1 hour at 0° C and 2 hours at room temperature; 8.8 parts of sodium hydroxide are added and the mixture is heated at 70° C for 4 hours. The alkaline reaction mixture is shaken with ether and the aqueous phase is acidified with a 2N solution of $H_2SO_4$ to a pH of 1 and then saturated with NaCl. After extraction with ether there are obtained 19.6 parts (41.3% of theory) of N-ethyl-N-n-butyl-3-amidosulfopropionic acid in the form of a white crystalline product, m.p. 67°–68° C.

| Analysis results | C | H | O | N | S | AN | SN |
|---|---|---|---|---|---|---|---|
| Found: | 45.7 | 7.9 | 27.3 | 6.3 | 13.2 | 234 | 349 |
| Calculated: | 45.6 | 8.0 | 27.0 | 5.9 | 13.5 | 236.5 | 236.5 |

EXAMPLE 24

N-n-dodecyl-3-amidosulfopropionic Acid

I. To 37 parts of n-dodecylamine and 300 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for 1 hour at 0° C and for 5 hours at room temperature; methanol is added and the precipitated methyl N-n-dodecyl-3-amidosulfopropionate is filtered off. There are obtained 49 parts of this ester.

II. The ester thus obtained is mixed with 200 ml of $H_2O$ and 6.65 parts of sodium hydroxide are added to the mixture and stirring is continued for 4 hours at 80° C. The reaction mixture is slurried in $H_2O$ and acidified with a 2N solution of $H_2SO_4$ to a pH of 1. The precipitate is filtered off, recrystallized from methanol and dried at 50° C/25 mm.

There are obtained 26.5 parts (41.2% of theory) of N-n-dodecyl-3-amidosulfopropionic acid in the form of a white crystalline product melting at 129°–133° C.

| Analysis results | C | H | O | N | S | SN | AN |
|---|---|---|---|---|---|---|---|
| Found: | 56.1 | 9.8 | 19.6 | 4.6 | 9.9 | 185 | 174 |
| Calculated: | 56.1 | 9.65 | 19.9 | 4.35 | 10.0 | 174.5 | 174.5 |

EXAMPLE 25

N-oleyl-3-amidosulfopropionic Acid

I. To 53.4 parts of oleylamine and 100 parts of water there are added dropwise at 0° C, with stirring, 18.65 parts of methyl 3-chlorosulfonylpropionate and then simultaneously from separate dropping funnels 18.65 parts of methyl 3-chlorosulfonylpropionate and 54 parts of 14.8% caustic soda solution. Stirring is continued for 1 hour at 0° C and for 0.5 hours at room temperature and there are obtained from the organic phase, after extraction with $CH_2Cl_2$, 34.6 parts (41.6% of theory) of methyl N-oleyl-3-amidosulfopropionate.

II. The resulting ester is saponified by stirring it for 4 hours at 80° C in 206 parts of 2.8% caustic soda solution. The reaction mixture is acidified with a 2N solution of $H_2SO_4$ to a pH of 1 and the precipitated acid is filtered off and recrystallized from 80% alcohol. There are obtained 18.3 parts (22.7% of theory) of N-oleyl-3-amidosulfopropionic acid as a waxy product.

| Analysis results | C | H | O | N | S | SN | AN |
|---|---|---|---|---|---|---|---|
| Found: | 64.0 | 10.4 | 14.5 | 3.8 | 6.6 | 123 | 121 |
| Calculated: | 62.5 | 10.15 | 15.9 | 3.5 | 7.95 | 139 | 139 |

EXAMPLE 26

N-stearyl-3-amidosulfopropionic Acid

I. To 134.5 parts of stearylamine and 1,200 parts of water there are added dropwise at 0° C, with stirring, 46.6 parts of methyl 3-chlorosulfonylpropionate and then simultaneously from separate dropping funnels 46.6 parts of methyl 3-chlorosulfonylpropionate and 135 parts of 14.8% caustic soda solution. Stirring is continued for a further hour at 0° C and 5 hours at room temperature; methanol is added and the precipitated methyl N-stearyl-3-amidosulfopropionate is filtered off.

II. The resulting ester is slurried with 200 parts of water, mixed with 20 parts of sodium hydroxide and stirred for 4 hours at 80° C. The reaction mixture is acidified with a 2N solution of $H_2SO_4$ to a pH of 1 and the precipitated N-stearyl-3-smidosulfopropionic acid is filtered off and recrystallized from methanol. There are obtained 59 parts (29.1% of theory) of a white crystalline product melting at 135°–138° C.

|  | C | H | O | N | S | SN | AN |
|---|---|---|---|---|---|---|---|
| Found: | 63.9 | 10.8 | 14.0 | 3.9 | 7.9 | 121 | 121 |
| Calculated: | 62.25 | 10.6 | 15.8 | 3.45 | 7.9 | 138.5 | 138.5 |

EXAMINATION OF THE PRODUCTS OF THE INVENTION a. Herbert Corrosion Test

The anticorrosive effect of an aqueous solution consisting of 1% of active ingredient and water of 10° German hardness (10° dH) is illustrated in the Herbert test system adopted in the metalworking and machining industry. This test involves a standardized cast iron plate and standardized steel chips having a length of 5 mm and available from Alfred Herbert, Coventry, England. Prior to carrying out the test, the square plate measuring 100 × 100 × 5 mm is carefully ground on a belt grinder using a corundum emery belt grade 120 and is then washed with white spirit and ethanol and dried with a clean cloth. The steel chips provided with the test kit and obtained under standardized conditions from a 0.40% carbon steel are then heaped onto the prepared cast iron plate by means of a suitable metal or plastic spoon having the capacity of a normal teaspoon to form 4 heaps located at equal distances from each other and from the edges of the plate. The heaps should be spread out into a single layer with the chips as close to each other as possible.

The solutions or emulsions to be tested for corrosion inhibition are dripped onto the chips by means of a graduated pipette in such an amount that the liquid reaching the cast iron plate is just prevented from spreading by the chips. After standing for 24 hours in an atmosphere of 70% relative humidity, the chips are tipped from the plate. The contours of the dried aqueous medium are distinctly visible on the plate. Depending on the anti-corrosive properties of the liquid, rust marks of various sizes are visible at the points of contact between the chips and the plate, and may even have formed an uninterrupted rust layer. The percentage area of rust may be assessed by eye.

b. Cast Iron Filter Test

Another corrosion test is the cast iron filter test. This involves the use of a Petri dish having an internal diameter of about 10 cm and a fitting cover. A black ribbon round filter is placed in the Petri dish. From 5 to 10 g of coarse cast iron chips GG 20 (DIN 1691) are distributed over the filter with a suitable spoon to give a uniform circle in the center of the filter, the periphery of this circle being at a distance of about 1.5 cm from the edge of the filter. The chips have a length of about 5–8 mm and must be prepared from clean cast iron GG 20 without the use of drilling oil or other cooling lubricants. All fine particles must be sieved off.

5 ml of the solution or emulsion to be tested for corrosion inhibition properties are evenly spread over the chips using a graduated pipette. The pH of the test liquid is noted, since this is an important factor for assessment. It may be adjusted to a specific standard value, for example 8.5. Following wetting of the chips, the cover is placed on the dish, which is then left to stand for 2 hours under normal laboratory conditions at from 23° to 25° C and about 70% relative humidity. The cover is then removed and the filter is quickly freed from the chips by placing it face-down on tap water. It is immediately sprayed and impregnated with an indicator solution of the following composition:

1 g of potassium hexacyanoferrate (III)
30 g of common salt
1 l of water.

The indicator is then allowed to act on the filter for 17 sec. in the air. The filter is then carefully rinsed with running drinking water and dried in air in a moderately warm place. This procedure results in brownish-yellow, yellow and/or bluish-green spots of various strength according to the anticorrosive properties of the medium, the brownish-yellow or yellow spots indicating poor anticorrosive properties. Optimum properties are indicated by the lack of any brownish-yellow or yellow spots with at the most only traces of pale bluish-green spots being present. The colorations are fast and the filters can therefore be used for documentation purposes. Grading may be as follows:

very poor: large spots of strong color, mainly yellowish-brown;
poor: large spots of strong color consisting of about equal proportions of yellowish-brown and bluish-green;
fair: spots of medium size and of paler color consisting of about equal proportions of yellow and bluish-green;
good: very pale spots of pin-head size, mainly bluish-green;
very good: no spots or at the most very few, very small spots of a pale bluish-green.

c. Foaming Behavior

The foaming behavior may be tested according to DIN 53,902 "Bestimmung des Schaumvermogens und der Schaumbestandigkeit" ("Determination of foamability and resistance to foaming"). The simplified test method is sufficient, in which the plunger holding the perforated plate is uniformly moved up and down by hand 30 times in 30 sec. and then carefully removed. The volume of the foam is read off in ml from the graduated foam cylinder after 1, 5 and 10 minutes. It is important to note the temperature, concentration and water hardness.

The following products were compared to illustrate the differences in effect in the above test methods (a) to (c):

Triethanolamine salts of:
1. N-(2-ethyl-n-hexyl)-3-amidosulfopropionic acid (1)
2. N-(3-phenyl-n-butyl)-3-amidosulfopropionic acid (2)
3. N-(phenylhexyl)-3-amidosulfopropionic acid (3) (isomer mixture)
4. N-benzyl-3-amidosulfopropionic acid (4)
5. N-(2-phenylethyl)-3-amidosulfopropionic acid (5)
6. N-(2-methyl-n-butyl)-3-amidosulfopropionic acid (6)
7. N-(2-methyl-n-but-3-ynyl)-3-amidosulfopropionic acid (7)
8. N-phenyl-3-amidosulfopropionic acid (8)
9. N,N-(di-2-ethyl-n-hexyl)-3-amidosulfopropionic acid (9)
10. N,N-(di-n-butyl)-3-amidosulfopropionic acid (10)
11. Oleate (11)
12. Oleoyl sarcoside (12)
13. Sodium salt of $C_{13-15}$ sulfonamido acetic acid (13)
14. Phenylsulfonylamidocaproic acid (14).

The test results are listed in the following Table. The water used had a hardness of 10° dH. The pH was adjusted to 8.5 by means of triethanolamine in the case of the triethanolamine salts and by means of caustic soda in the case of the sodium salt (12). It should be noted that the cast iron filter test is generally more sensitive and that the results of both tests do not always agree. However, good to very good results in both tests usually indicate good behavior in industrial practice.

Of the agents of the invention (1–10), all show excellent non-foaming properties and the substances 1, 3 and 9 also show good to very good anticorrosive properties. They are superior to the comparative substances 11 to 14 of the prior art in this combination of properties. However, the agents 2, 5 and 10 of the invention also indicate that even though they require a somewhat higher concentration for good anticorrosive effect they may nevertheless, on account of their inherent low-foaming properties, be of advantage over the comparative products when used in industrial recipes. The other agents of the invention (4, 6, 7 and 8) of poor anticorrosive properties merely demonstrate very low-foaming properties but would seem either not to have the optimum chemical structure or not to possess the optimum molecular weight for the formation of an anticorrosive adsorption layer on the metal surface.

TABLE

| No. | pH | Conc. (g/l) | Product Anticorrosive properties (25° C, 10° dH) | | Foaming behavior (25° C, 2 g per liter, 10° dH) (ml of foam) | | |
|---|---|---|---|---|---|---|---|
| | | | (c) Herbert test rust areas (%) | (b) cast iron test | 1 minute | 5 minutes | 10 minutes |
| 1 | 8.5 | 10 | 0 | very good | 0 | 0 | 0 |
|   |     | 30 | 0 | very good |   |   |   |
| 2 | 8.5 | 10 | 0 | poor | 10 | 0 | 0 |
|   |     | 30 | 0 | very good |   |   |   |
| 3 | 8.5 | 10 | 0 | good | 0 | 0 | 0 |
|   |     | 30 | 0 | very good |   |   |   |
| 4 | 8.5 | 10 | 30 | poor | 0 | 0 | 0 |
|   |     | 30 | 20 | fair to good |   |   |   |
| 5 | 8.5 | 10 | 15 | fair | 0 | 0 | 0 |
|   |     | 30 | 5 | very good |   |   |   |
| 6 | 8.5 | 10 | 100 | very poor | 5 | 0 | 0 |
|   |     | 30 | 100 | very poor |   |   |   |
| 7 | 8.5 | 10 | 100 | very poor | 0 | 0 | 0 |
|   |     | 30 | 100 | very poor |   |   |   |
| 8 | 8.5 | 10 | 100 | very poor | 0 | 0 | 0 |
|   |     | 30 | 40 | very poor |   |   |   |
| 9 | 8.5 | 10 | 5 | very good | 0 | 0 | 0 |
|   |     | 30 | 0 | very good |   |   |   |
| 10 | 8.5 | 10 | 18 | good | 0 | 0 | 0 |
|    |     | 30 | 5 | very good |   |   |   |
| 11 | 8.5 | 10 | 10 | fair to good | 130 | 80 | 70 |
|    |     | 30 | 0 | nearly very good |   |   |   |
| 12 | 8.5 | 10 | 0 | very good | 45 | 25 | 15 |
|    |     | 30 | 0 | very good |   |   |   |
| 13 | 8.5 | 10 | 0 | fair to good | 25 | 15 | 10 |
|    |     | 30 | 0 | good to very good |   |   |   |
| 14 | 8.5 | 10 | 0 | fair to good | 25 | 15 | 5 |
|    |     | 30 | 0 | very good |   |   |   |

We claim:

1. A compound of formula I

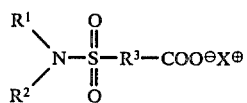

wherein $R^1$ denotes straight-chain or branched-chain, saturated or olefinically or acetylenically unsaturated alkyl of from 1 to 18 or 3 to 18 carbon atoms respectively, corresponding alkyl substituted by a methoxy or ethoxy group, cycloalkyl of from 5 to 12 ring members, phenyl, phenyl substituted by $C_{1-3}$ alkyl, methoxy or ethoxy groups or halogen atoms, or phenylalkyl of from 1 to 5 carbon atoms in the alkyl group, $R^2$ denotes hydrogen or $R^1$, $R^1$ and $R^2$ form, together with the nitrogen atoms, a piperidine, pyrrolidine or morpholine ring, $R^3$ denotes alkylene of from 2 to 5 carbon atoms, and $X^+$ denotes an alkali metal or ammonium cation or proton.

2. A compound as set forth in claim 1 wherein $R^1$ denotes methyl, ethyl, n-propyl, isopropyl, n-butyl, isobutyl, n-hexyl, n-octyl, hexyl, 2-ethylhexyl, methoxyethyl, cyclohexyl, n-dodecyl, stearyl, oleyl, 2-methylbutyn-2-yl, phenyl, tolyl, anisidyl, phenetidyl, benzyl, phenylethyl, phenyl-n-butyl or phenyl-n-hexyl, $R^2$ denotes hydrogen or the same or a different $R^1$, and $R^1$ and $R^2$ form, together with the nitrogen atom, the piperidine, pyrrolidine or morpholine ring.

3. A compound as set forth in claim 1 wherein $R^3$ denotes ethylene, propylene, butylene or isobutylene.

4. A compound as set forth in claim 1 wherein $X^-$ denotes a cation of mono-, di- or trimethylamine, mono-, di- or triethylamine, mono-, di- or triethylamine, mono-, di- or triisopropylamine, mono-, di-, or triisopropylamine, mono-, di- or triisobutylamine, 2-methoxyethylamine, 3-methoxypropylamine, 2-ethylhexylamine, mono-, di- or triethanolamine, 3-aminopropanol, cyclohexylamine, N,N-dimethylcyclohexylamine, morpholine, pyridine, quinoline, ethylenediamine, diethylenetriamine, pentaethylenehexamine or the corresponding ethoxylated or propoxylated primary amines.

* * * * *

UNITED STATES PATENT AND TRADEMARK OFFICE
CERTIFICATE OF CORRECTION

PATENT NO. : 4,060,522
DATED : November 29, 1977
INVENTOR(S) : KINDSCHER ET AL

It is certified that error appears in the above-identified patent and that said Letters Patent are hereby corrected as shown below:

In claim 1, column 19, line 49, cancel "X+" and substitute --$X^{\oplus}$--.

In claim 4, column 20, line 39, delete "X-" and substitute --$X^{\ominus}$--; line 40, cancel "mono-", second occurrence, and substitute --mono-,--; line 41, cancel ", di-", first occurrence, and substitute --di- --; line 41, delete "triethylamine,", second occurrence; line 42, cancel "mono-, di- or", first occurrence; line 42, cancel "triiso-"; line 43, cancel "propylamine, mono-, di- or".

Signed and Sealed this

Twenty-fourth Day of April 1979

[SEAL]

Attest:

RUTH C. MASON
Attesting Officer

DONALD W. BANNER
Commissioner of Patents and Trademarks